US00PP10068P

Jnited States Patent [19]

.amb et al.

[11] Patent Number: Plant 10,068

[45] Date of Patent: Oct. 14, 1997

[54] ANTHURIUM PLANT NAMED ELECTRON

[75] Inventors: Ann E. Lamb, Sebring; Robert D. Hartman, Lake Placid, both of Fla.

[73] Assignee: Twyford International, Inc., Santa Paula, Calif.

[21] Appl. No.: 629,770

[22] Filed: Apr. 9, 1996

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

An Anthurium plant named 'Electron' having small red spathes with a purple spadix, with the spathes being carried above and among the foliage. The leaves are small, very dark green, and very shiny. The plant has a miniature growth habit, and is suitable for smaller pot sizes (10 cm). The plant grows to a marketable size and begins flowering quickly.

1 Drawing Sheet

The present invention comprises a new and distinct cul-/ar of Anthurium, botanically known as *Anthurium hybrid,* ıd referred to by the cultivar name 'Electron'.

The new cultivar is a product of a breeding program rried out by the inventors Ann E. Lamb and Robert D. artman in Apopka and Sebring, Fla., and is the result of the llowing cross made in Apopka, Fla. in February 1993: An ınamed *Anthurium hybrid* identified by proprietary code ımber ×Anthurium '94-4', disclosed in U.S. Plant Pat. No. 820.

The cultivar was discovered from the progeny of the ıted cross in March 1995 by Ann E. Lamb. Tissue culture rformed by or under the supervision of Ann E. Lamb at bring, Fla. was used to increase the number of plants for aluation and has demonstated the stability of the combi-tion of characteristics of 'Electron' from generation to neration.

The following observations, measurements and values scribe plants grown in Homestead, Fla. under shade house nditions which closely approximate those generally used horticulture practice.

The following traits have been repeatedly observed to be aracteristics which in combination distinguish, 'Electron' ım other Anthuriums of the same general type, for ample, the unpatented cultivar 'Lady Jane' to which mparative reference is made.

1. The plant produces many small red spathes, with a rple spadix, with the spathes being carried above and ıong the foliage.

2. The leaves are small, very dark green, leathery, and ry shiny.

3. The growth habit is very branched and compact, ıking 'Electron' suitable for smaller pot sizes.

4. The plant grows to a marketable size and begins wering quickly.

5. The spathe color actually darkens as the spathe matures, important feature to the ultimate consumer.

Compared to 'Lady Jane', 'Electron' has a compact, ghly branched, miniature growth habit. The inflorescence 'Electron' are red, abundantly produced, and smaller than ıse of 'Lady Jane'. Also, plants of 'Electron' grow to a rketable size and begin flowering earlier than 'Lady ıe'.

All color references are measured against The Royal rticultural Society Color Chart. Colors are approximate color depends on horticultural practices such as light level l fertilization rate, among others, without, however, any iance in genotype.

The color photographic drawing comprises a top perspective view of the inflorescence and foliage of a plant of 'Electron' in a 15.3 cm pot approximately 10 months after planting a 20 week old liner obtained by tissue culture and grown under appropriate growing conditions.

Colors are as accurate as possible with color illustrations of this type.

Origin: Seedling selected from a cross of an unnamed Anthurium hybrid identified by a proprietary code number × Anthurium '94-4'.

Classification: *Anthurium hybrid,* cv. 'Electron'.

Propagation: Asexual propagation either by tissue culture or division.

INFLORESCENCE

Immature: The spathe is tightly rolled around the spadix and emerges from the petiole sheath. The spathe is fully open approximately when the peduncle is fully elongated, approximately 19.5 cm to 23 cm above the soil surface. The color of the flower peduncle is 146 C flushed with 175 A.

Mature:

*Color.*—Fully open: Upper surface: Redder than, but closest to 45 D. Lower surface: 47 A. Faded: Upper surface: 46 B. Lower surface: 47 A.

*Arrangement.*—The inflorescence terminates from a straight or often curved wiry peduncle and opens vertically among or above the leaves.

*Shape.*—The spathe is ovate with a cordate base and a cuspidate tip. The spathe typically has a wavy margin.

*Size.*—The fully expanded spathe is approximately 3.8 cm to 4.6 cm long and approximately 2.4 cm to 2.7 cm in width.

*Flowering time.*—After approximately 10 months from a 20 week old liner for an untreated plant as illustrated in the photograph and depending on season, approximately 4 to 7 blossoms will be present. Smaller blooms may occur on less mature growth. First flowers have been observed in 20 week old finished liners.

REPRODUCTIVE ORGANS

Spadix:

*Size.*—Approximately 2.7 cm to 3.3 cm in height and approximately 5 mm in width.

*Color.*—When the spathe unrolls, the spadix is 76 A-B at the base, 186 A in the center, and 59 D at the tip.

*Stamens.*—Anthers and filaments are minute and not clearly visible. Pollen is white in color.

*Pistil.*—Translucent white, protruding between the staminate flowers, firmly fixed to the main axil. The pistilate flowers extend approximately 0.2 mm beyond the staminate flowers.

General appearance: Under appropriate growing conditions, 'Electron' reaches a size of approximately 14 cm to 16 cm in height and approximately 37 cm to 40 cm in width.

Leaves:

*Form.*—The leaf blade is ovate with an acute tip and a truncate to slightly cordate base. The midrib is straight over the length of the leaf, and often curved downward at the tip. The leaf margins are somewhat wavy. The leaf blade is leathery in texture, with a very shiny surface.

*Size.*—Leaf blades of a mature size plant are approximately 13 cm to 15 cm in length and approximately 7.4 cm to 9 cm in width measured at the widest point.

*Veins.*—The veins are sunken, with the leaf blade noticeably convex between veins on the upper surface. The midrib protrudes from the upper surface of the leaf for approximately ⅔ the length of the leaf. Well defined primary veins on leaves radiate out from the juncture of the petiole and the leaf. Veins stand out prominently on the lower side. There are approximately 4–6 primary veins on the leaf.

*Petiole.*—The petiole is approximately 10 cm to 12 cm in height from the base of the petiole to the base of the leaf blade on the primary shoot. The petiole is approximately 3.2 mm in diameter just below the geniculum. The petiole below the geniculum is straight. Secondary shoots are somewhat smaller depending on the age of the shoot.

*Petiole wings.*—Petiole wings are approximately 1.2 cm to 1.7 cm in length and approximately 2.5 mm in width at their midpoint. The tip of the petiole wings is rounded. There is approximately 9.4 cm between the top of the wing and the base of the geniculum.

*Geniculum.*—The geniculum is approximately 1.7 cm to 1.9 cm in length, approximately 4.0 mm in diameter, and is often curved. The geniculum is somewhat indistinct.

*Lobes.*—The leaf has two lobes which do not extend past the petiole. The distance from the petiole/leaf juncture to the highest point on the blade is approximately 4.4 cm to 5.2 cm.

*Colors.*—Upper surface: Much darker and greener than, but closest to 147 A. Newly expanded leaves are flushed with bronze 175 A. Lower surface: 146 B. Midrib, upper surface: 146 C. Midrib, lower surface: 146 D. Petiole: 146 B, flushed with 175 A when exposed to bright light. Petiole wing: 146 D, occasionally streaked with 183 A. Leaf Sheath: 146 D, streaked with 183 A. Geniculum: 146 D.

Roots: White fleshy roots with fine laterals. The roots are 180 B in color when produced above the soil and exposed to light.

I claim:

1. A new and distinct cultivar of Anthurium plant named 'Electron', as illustrated and described.

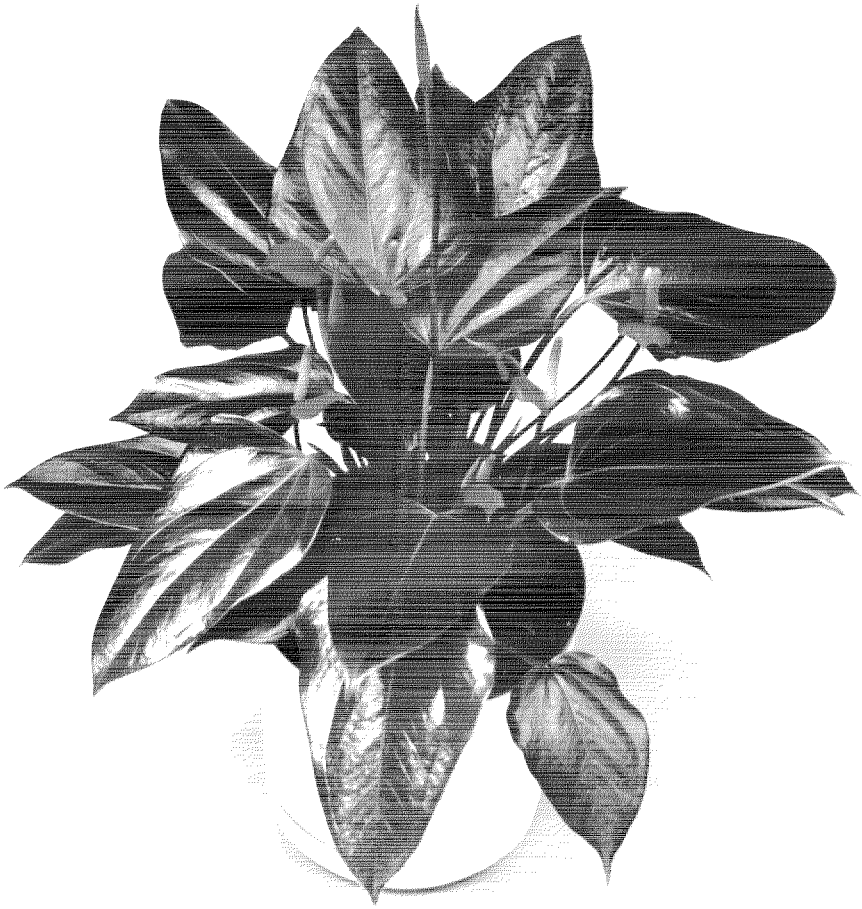

* * * * *